United States Patent [19]

Gehrken et al.

[11] 4,062,871

[45] Dec. 13, 1977

[54] PROCESS FOR THE DESUBLIMATION OF PHTHALIC ANHYDRIDE

[75] Inventors: Hubert Gehrken, Ahe; Gerhard Keunecke, Geyen, both of Germany

[73] Assignee: Chemiebau Dr. A. Zieren Gesellschaft Mit Beschraenkter Haftung & Co. KG, Cologne, Germany

[21] Appl. No.: 549,998

[22] Filed: Feb. 14, 1975

Related U.S. Application Data

[63] Continuation of Ser. No. 422,903, Dec. 7, 1973, abandoned.

[51] Int. Cl.² .......................................... C07D 307/89
[52] U.S. Cl. ............................ 260/346.4; 260/346.7; 23/264
[58] Field of Search ........................ 260/346.4, 346.7

[56] References Cited

U.S. PATENT DOCUMENTS 3,471,521  10/1969  Junker ........................ 260/346.4
3,869,479  3/1975  Barth et al. ................... 260/346.4

Primary Examiner—Henry R. Jiles
Assistant Examiner—Bernard Dentz
Attorney, Agent, or Firm—Millen & White

[57] ABSTRACT

In a process for the separation of phthalic anhydride from reaction gas obtained from the catalytic air oxidation of o-xylene which comprises cooling the gas in a separator in indirect heat exchange relationship with cooling surfaces inside the separator maintained at 45°–65° C, withdrawing residual reaction gas through a gas outlet and melting off resultant desublimated phthalic anhydride from the cooling surfaces by heating the latter to a temperature in the range of 150°–250° C, the improvement wherein heat is applied to an external surface of the separator adjacent said gas outlet during the cooling of the gas inside the separator, said heat being sufficient to prevent a buildup of non-meltable impurities on the cooling surface inside said separator and adjacent to said gas outlet.

7 Claims, 2 Drawing Figures

PROCESS FOR THE DESUBLIMATION OF PHTHALIC ANHYDRIDE

This is a continuation of application Ser. No. 422,403, filed Dec. 7, 1973 and now abandoned.

BACKGROUND OF THE INVENTION

This invention relates to a system for the separation of phthalic anhydride from the reaction gas resulting from the catalytic oxidation of o-xylene with air.

Phthalic anhydride is conventionally formed by the gas phase oxidation of o-xylene with air in the presence of $V_2O_5$ catalysts. The resultant reaction gas is passed to a separator where the phthalic anhydride is precipitated onto relatively cold pipes which are then heated to melt-off the precipitate. For the separation and melting off of the phthalic anhydride, the tubes are periodically cooled to a temperature in the range of 45°-65° C and heated to a temperature in the range of 150°-250° C, respectively. Such separators contain a large number of rows of tubes around which the reaction gas flows during the precipitation phase. During the continuous operation of these separators, it has now been found that the tube bundles last surrounded by the flowing reaction gas, i.e., the tubes on the gas outlet side of the separator, are gradually covered with deposits which, in contrast to the phthalic anhydride, can no longer be removed by melting with the use of the aforementioned heating temperatures. Because of this buildup, the flow resistance of the separator on the gas side increases by a multiple, and the separation efficiency which, in a separator without such deposits, is at above 99% of the physically separable matter, drops to 97%. This, in turn, results in a substantially increased load or even overload in the following waste gas purification stage. Still further, deposits result in an erosion and corrosion of the tubes and/or fins of the separator. Finally, in time, these difficult to melt deposits become so thick that the operation must be interrupted and the fouled tube bundles must be cleaned by hand. Thereafter, the tubes are subjected to repeated flushing with a suitable scrubbing, e.g. solution of sodium hydroxide. Such interruptions in the continuous process are highly undesirable since an additional separator must be kept in reserve for exchange purposes. Moreover, a complete elimination of the deposits is impossible, so that the next cleaning operation must be conducted after an even shorter operating period.

SUMMARY

A principal object of this invention, therefore, is to provide an improved system, including a new process and new apparatus for eliminating substantially, if not completely, the deposition of these difficult to remove deposits.

Upon further study of the specification and appended claims, other objects and advantages of this invention will become apparent.

To achieve these objects, it has now been discovered that the aforementioned operational drawbacks can be avoided according to the present invention by providing heating means in the gas-collecting section located on the gas outlet side of a conventional separator, and during the cooling period when the phthalic anhydride is precipitated maintaining the gas-collection section at a sufficiently high temperature to prevent such non-meltable deposits from accumulating on the tubes of the regenerator, especially on the gas outlet side. It has been unexpectedly discovered that the formation of deposits on the tubes on the exit side of a separator, with all the disadvantages connected therewith, was avoided by maintaining the gas-collecting section at a temperature of 150°-250° C during the cooling period. After operating for 3½ years, no deposits could be detected in the separator. There was no corrosion or erosion, and the separation efficiency was unchanged at 99% after this operating time. Preferably, the gas-collecting section is held, during the cooling phases, at a temperature in the range of 170°-210° C, especially 190°-200° C.

It is our understanding that the invention works in a way as described herebelow although the invention is not limited to this explanation.

Without heating the gas collection section as provided according to the invention deposits are formed on the internal surface area thereof. These deposits contain volatile products of the catalytic oxidation which (1) have passed the cooling section of the separator during the cooling phases without being precipitated and (2) have been evolved during the melting-off phases from the melting deposits. These deposits consist mainly of maleic anhydride, maleic acid, phthalic acid and phthalic anhydride. From time to time during a heating phase of the tubes these deposits grown to a thick shell are loosened as a block and fall down onto the uppermost tubes where the block begins to melt. Several heating phases are necessary to melt down the block resting on these tubes. As the melt so formed is in contact with the hot tubes, maleic acid is rearranged to fumaric acid which forms the permanent deposit on the upper tubes.

When the gas collection section is heated according to this invention the volatile components are not condensed in the dome but can escape from the condenser as a gas. Thus, the uppermost tubes cannot come into contact with said mixture containing maleic acid either in solid or liquid form so that formation of permanent deposits is avoided.

Apart from the elimination of the formation of deposits, the process of the present invention affords the additional advantage that, as compared to the previous mode of operation, considerably lower amounts of water and impurities are precipitated together with the phthalic anhydride. Accordingly, the melted-off crude phthalic anhydride contains less phthalic acid and maleic acid, whereby the subsequent purification is facilitated and the losses incurred during this step are reduced.

The temperature of the reaction gas, upon entering the separator, is 145°-200° C, preferably 165°-175° C. The gas temperature, when the gas leaves the separator, is 55°-65° C. The temperature of 55°-65° C is obtained by cooling the reaction gas around the condenser tubes. The heated dome of the invention brings about only a small increase of the gas temperature which is on the order of 1° to 2° C.

The phthalic anhydride concentration in the reaction gas entering the separator is approximately 37–48 g./Nm³.

The apparatus for conducting the process comprises a housing with rows of tube bundles disposed therein and charged with a fluid heat transfer agent, which rows are surrounded by the flow of the phthalic anhydride-containing gases. The housing has openings for the entrance and exit of the gases and for discharging the melted-off phthalic anhydride. The improvement to such apparatus according to the invention, is heating means are provided in the wall of the gas-collecting dome disposed on the gas outlet side of the housing. Preferably, this dome wall is provided on its outside with external heat exchange tubes, and can be heated separately and independently of the tube bundles inside the separator so that the external tubes can be heated during the cooling period to maintain a temperature in the range of 150°-250° C, preferably 190°-200° C, at the inside wall of the dome. Of course, in place of the tubes it is also possible to utilize a heating jacket, or electrically wire heating elements, or any other conventional heating means.

The process of this invention can be conducted in all types of separators independent of their geometry. The important point is that the housing section serving for collecting the gas for discharge through the gas outlet pipe is maintained even during the cooling phase at a sufficiently elevated temperature, experience with the depicted separator indicating a temperature in the range of 150°-250° C. In each separator the uppermost dome has to be kept on 150°-250° C to avoid solid deposits or liquid condensate to be formed in the dome. It is not necessary for the gas exit pipe to be connected to the dome. If the gas inlet pipe is led to the dome and the exit pipe is connected to the bottom of the separator only that part of volatile compounds evolved during the melting-off periods from the melting deposits and rising in the separator are precipitated in the dome. In this case although the deposits grow slower than with upward gas flow the same problem exists.

Generally one can say that those parts of the separator case section extending above the upper tubes have to be kept in said temperature range in order to avoid solid deposits formed on the inside to fall down or liquid condensate to drop down onto the hot upper tubes.

DETAILED DESCRIPTION OF DRAWING

Figure 1:
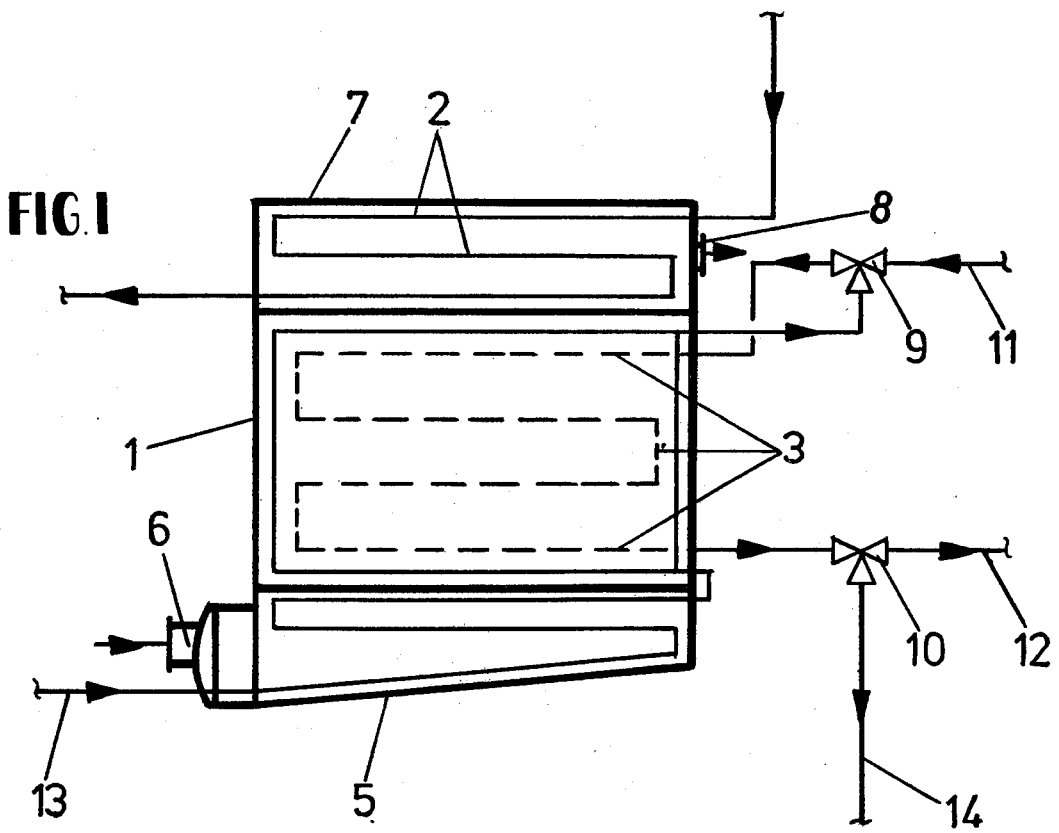
FIG. 1 is a vertical sectional schematic view of the separator for the process of this invention in a schematic representation.
Figure 2:
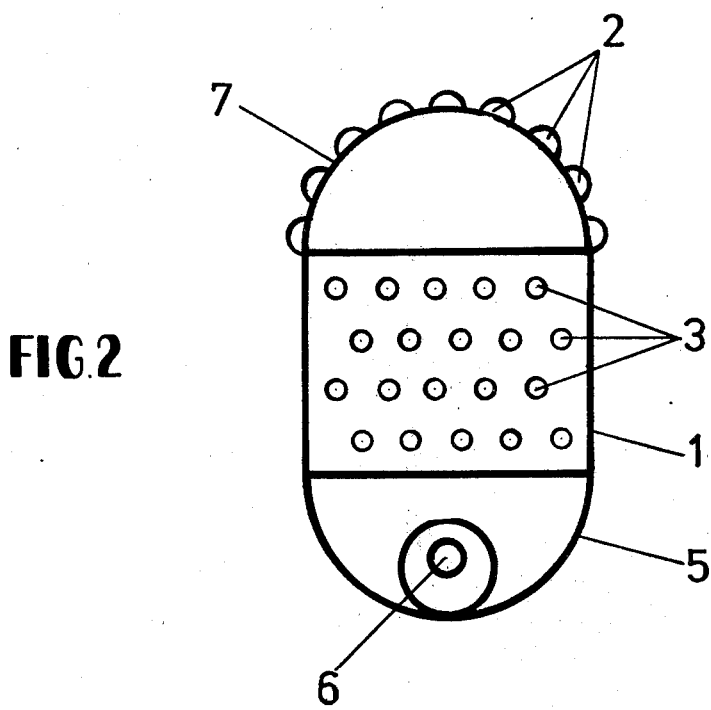
FIG. 2 is a schematic cross section of the separator.

The separator comprises a central housing section 1, a trough 5 with the gas inlet pipe 6 and a dome 7 with the gas outlet pipe 8. A system of finned tubes 3 is provided in the housing, this system being shown schematically in FIG. 1. On the outside, the wall of the gas-collecting dome 7 carries external heat exchange tubes 2 through which a fluid heat exchanger medium can be conducted in accordance with the direction of the arrow (FIG. 1), so that the interior of the dome is maintained at the desired temperature. In order to switch the finned tube system 3 from coolant to heating medium and vice versa, valves 9, 10 are provided. During the cooling phase, the coolant is fed at 11, flows through the finned tubes in the direction of the conduit shown in dashed lines, and exits at 12. During this time, the pipelines 2 are charged with a heating medium. In order to melt off the phthalic anhydride precipitated on the finned tubes 3, the valves 9 and 10 are switched over, so that the heating medium supplied at 13 is returned, after flowing through the external heating unit shown in full lines via valve 9, into the separator, and after passing through the tube system shown in dashed lines, the heating medium is withdrawn at 14.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

COMPARATIVE EXAMPLE 1

A reaction gas obtained by the catalytic oxidation of o-xylene with air is conducted through a separator, the finned tubes of which are charged with a coolant having a temperature of 55° C. The flow of the heating fluid, having a temperature of 195° C, through the pipelines of the gas-collecting dome is interrupted at the beginning of the cooling phase. Therefore, the temperature of the fluid drops during the cooling phase to about 70° C. In order to melt off the thus-precipitated phthalic anhydride, the separator tubes as well as the pipelines of the gas-collecting dome have a heating fluid of 195° C flowing therethrough.

After an operating period of about 1 year, thick deposits of difficult to melt compounds had formed on the tubes disposed closest to the gas outlet. The flow resistance on the gas side had risen from 250 mm. $H_2O$ to 750 mm. $H_2O$, and the separation efficiency had decreased from 99.2 to 97.0%. The crude phthalic anhydride melted off from the separator contained 95.5 to 96.1% by weight of phthalic anhydride; 3.6–4.0% by weight of phthalic acid; and 0.3–0.5% by weight of by-products.

COMPARATIVE EXAMPLE 2

The procedure of Comparative Example 1 was followed, except that the temperature of the heating medium for the gas-collecting dome was maintained at about 140° C (heating with saturated steam of 3 atm. gauge) during the cooling phase as well as during the melting-off phase. After about 1½ years, the same difficulties occurred as in Comparative Example 1. The crude product melted off from the separator consists of 96.3–97.0% by weight of phthalic anhydride, 2.8–3.4% by weight of phthalic acid, and 0.2–0.3% by weight of by-products.

EXAMPLE 1

A reaction gas obtained by the catalytic air oxidation of o-xylene is conducted through a separator, the finned tubes of which are cooled with a cooling fluid at 55° C. Simultaneously, the gas-collecting dome, provided with external tubing, is heated with a heating fluid of 190° C. During the melting-off step, the finned tubes as well as the pipelines of the gas-collecting dome were heated with a heating fluid at 190° C. After an operating period of 3½ years, no deposits whatever were detected in the separator. There was no corrosion or erosion. The flow resistance on the gas side is practically unchanged; the degree of efficiency of the separator is unaltered at 99%. The molten crude product consists of 98.6–99.1% by weight of phthalic anhydride, 0.8–1.2% by weight of phthalic acid, and 0.1–0.2% by weight of by-products. The solidification point of the crude product is 130.3° C.

EXAMPLE 2

The procedure of Example 1 is followed, except that the gas-collecting dome is heated with a heating fluid of 170° C. After an operating period of 3½ years, no deposits can be determined in the separator. The crude melted-off product from the separator contains 98.4-98.7% by weight of phthalic anhydride, 1.1-1.3% by weight of phthalic acid, and 0.2-0.3% by weight of by-products.

EXAMPLE 3

The separator was operated as in Example 1, but the gas-collecting dome was heated to 220° C with a heating fluid. After 3½ years of operation, no deposits could be detected. The melted-off crude product contains 98.8-99.1% by weight of phthalic anhydride, 0.8-1.0% by weight of phthalic acid, and 0.1-0.2% by weight of by-products.

The comparative examples demonstrate that when the heating medium temperature for heating the dome is less than 150° C, substantial deficiencies can be observed during the continuous operation of the separator. In case of heating medium temperatures of above 250° C, these deficiencies do not occur, either, but greater heat losses are incurred which generally should be avoided. Furthermore, undesired thermal stresses occur in case the temperature differences between the central housing section and the gas-collecting dome become too great.

In a typical example the separator used in the process of the invention is 5.11 m long; 2.20 m broad and 3.41 m high. It contains 165 tubes with each 9.18 m² surface. The total tube surfaces are approx. 1500 m².

The preceding examples can be repeated with similar success by substituting the generically or specifically described reactants and/or operating conditions of this invention for those in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process of the separation of phthalic anhydride from reaction gas obtained from the catalytic air oxidation of o-xylene which comprises cooling the gas in a separator in indirect heat exchange relationship with tubular cooling surfaces inside the separator maintained at 45°-60° C., collecting and withdrawing residual reaction gas through a gas outlet and melting off resultant desublimated phthalic anhydride from the cooling surfaces by heating the latter to a temperature in the range of 150°-250° C. said separator having a separator case section extending above the uppermost tubular cooling surfaces, the improvement wherein the internal surface of said separator case section extending above the uppermost tubular cooling surfaces is maintained during the cooling of the gas inside the separator at a temperature of 150°-250° C. to prevent a buildup of non-meltable impurities on said uppermost tubular cooling surfaces.

2. A process as defined by claim 1 wherein said separator case section is dome-shaped.

3. A process according to claim 1 wherein the separator case section is maintained, during the cooling of the gas, at 170°-210° C.

4. A process according to claim 1 wherein the separator case section is maintained, during the cooling of the gas, at 190°-200° C.

5. A process as defined by claim 1 wherein said separator case section is maintained at a temperature of 150°-250° C during the cooling of the gas inside the separator by applying heat to the external surface of said gas collecting section.

6. A process according to claim 5 wherein the separator case section is maintained during the cooling of the gas at 170°-210° C.

7. A process according to claim 5 wherein the separator case section is maintained during the cooling of the gas at 190°-200° C.

* * * * *